US010624708B2

(12) United States Patent
Hunter

(10) Patent No.: US 10,624,708 B2
(45) Date of Patent: Apr. 21, 2020

(54) AUTO CABLE TENSIONING SYSTEM

(71) Applicant: Ethicon LLC, Guaynabo, PR (US)

(72) Inventor: Morgan Hunter, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 76 days.

(21) Appl. No.: 15/794,467

(22) Filed: Oct. 26, 2017

(65) Prior Publication Data
US 2019/0125463 A1 May 2, 2019

(51) Int. Cl.
*A61B 34/00* (2016.01)
*A61B 34/30* (2016.01)
*A61B 17/00* (2006.01)
*A61B 17/29* (2006.01)

(52) U.S. Cl.
CPC .............. *A61B 34/71* (2016.02); *A61B 34/30* (2016.02); *A61B 2017/00323* (2013.01); *A61B 2017/2901* (2013.01); *A61B 2017/2946* (2013.01); *A61B 2034/301* (2016.02); *A61B 2034/305* (2016.02); *A61B 2034/715* (2016.02); *Y10S 901/25* (2013.01)

(58) Field of Classification Search
CPC ......... A61B 34/30; A61B 34/73; A61B 46/10; A61B 2034/305; A61B 2017/00477
See application file for complete search history.

(56) References Cited

U.S. PATENT DOCUMENTS

| 4,688,555 | A | 8/1987 | Wardle | |
|---|---|---|---|---|
| 8,831,782 | B2 | 9/2014 | Itkowitz | |
| 8,931,682 | B2* | 1/2015 | Timm | A61B 17/072 227/178.1 |
| 9,216,061 | B2* | 12/2015 | Mohr | A61B 18/24 |
| 2003/0135204 | A1 | 7/2003 | Lee et al. | |
| 2010/0249759 | A1* | 9/2010 | Hinman | A61B 1/008 606/1 |

(Continued)

FOREIGN PATENT DOCUMENTS

| WO | 2014/151621 | 9/2014 |
|---|---|---|
| WO | 2014/151952 | 9/2014 |

OTHER PUBLICATIONS

International Search Report in corresponding PCT Application PCT/US2018/056403, completed Nov. 30, 2018 and dated Dec. 10, 2018.

(Continued)

*Primary Examiner* — Zakaria Elahmadi
(74) *Attorney, Agent, or Firm* — Vorys, Sater, Seymour and Pease LLP

(57) ABSTRACT

A surgical tool includes a drive housing, an elongate shaft that extends from the drive housing, and a plurality of drive cables extending within the elongate shaft between the drive housing and the end effector. A cable tensioner includes an inner hub and a cable guide assembly, and the cable guide assembly includes a central body arranged on the inner hub, and a plurality of cable guides arranged on the inner hub and engageable with the plurality of drive cables. Each cable guide is arranged to engage a corresponding one of the plurality of drive cables, and one or more biasing devices are engageable with the central body to bias the plurality of cable guides into constant engagement with the plurality of drive cables and thereby maintain constant tension in the plurality of drive cables.

20 Claims, 8 Drawing Sheets

(56) References Cited

U.S. PATENT DOCUMENTS

| | | | |
|---|---|---|---|
| 2012/0101495 A1* | 4/2012 | Young | A61B 17/29 606/41 |
| 2012/0298379 A1* | 11/2012 | Van Riet | E21B 43/103 166/382 |
| 2013/0041371 A1* | 2/2013 | Yates | A61B 17/07207 606/45 |
| 2013/0144306 A1* | 6/2013 | Stefanchik | A61B 17/29 606/130 |
| 2014/0005718 A1* | 1/2014 | Shelton, IV | A61B 17/07207 606/205 |
| 2014/0128849 A1 | 5/2014 | Au et al. | |
| 2015/0105798 A1* | 4/2015 | Lohmeier | A61B 34/71 606/130 |
| 2015/0257842 A1* | 9/2015 | Dachs, II | A61B 34/37 606/130 |
| 2015/0313676 A1 | 11/2015 | Deodhar | |
| 2016/0235490 A1* | 8/2016 | Srivastava | A61B 34/30 |
| 2016/0287252 A1 | 10/2016 | Parihar | |
| 2018/0242991 A1* | 8/2018 | Beira | A61B 17/29 |

OTHER PUBLICATIONS

Written Opinion in corresponding PCT Application PCT/US2018/056403, completed Nov. 30, 2018 and dated Dec. 10, 2018.

* cited by examiner

AUTO CABLE TENSIONING SYSTEM

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint on the instrument, which creates a more natural hand-like articulation.

To facilitate the wrist joint, robotic systems typically include cable driven motion systems designed to articulate (move) the instrument's end effector. Common cable driven motion system include one or more drive cables (alternately referred to as elongate members or wires) that extend through the wrist joint to aid in articulating the instrument's end effector. During use and over the life of the cable driven motion system, the cables will tend to fatigue in the form of stretch, creep, and slackening. Such cable fatigue can create backlash in the drive mechanism that often must be electrically or mechanically compensated for.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgery systems and, more particularly, to methods and systems of maintaining proper drive cable tension in cable driven motion systems used in robotic surgery.

The embodiments disclosed herein describe a cable tensioner used in cable driven robotic surgical tools. The cable tensioner is designed to maintain constant tension in the drive cables by constantly biasing a plurality of cable guides into engagement with the drive cables. This autonomously compensates for any stretch, slack, and/or creep that may develop in the drive cables over time or through prolonged use of the robotic surgical tools. The cable tensioner also includes various embodiments of a one-way locking mechanism designed to counteract back driving loads that may occasionally be applied by the drive cables against the cable guides. The one-way locking mechanism helps to maintain constant tension in the drive cables, thereby ensuring predictable drive performance in the robotic surgical tool.

Figure 1:
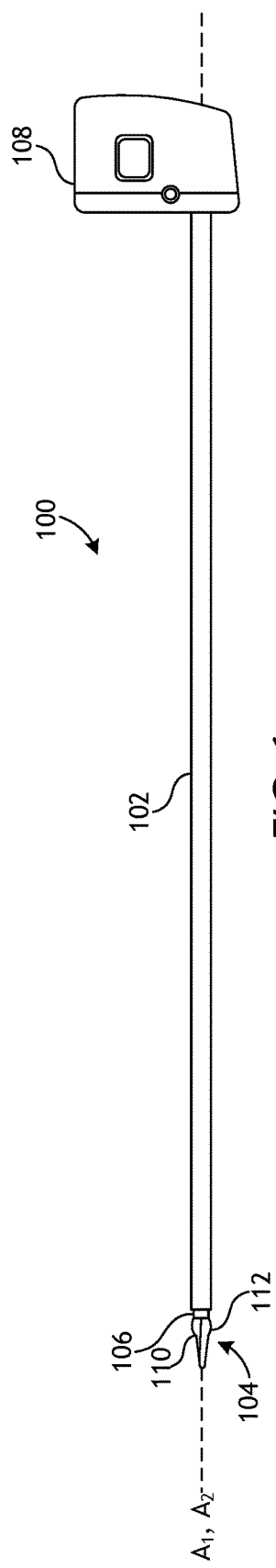
FIG. 1 is a side view of an example surgical tool that may incorporate some or all of the principles of the present disclosure.

FIG. 1 is side view of an example surgical tool 100 that may incorporate some or all of the principles of the present disclosure. As illustrated, the surgical tool 100 includes an elongate shaft 102, an end effector 104, a wrist 106 that couples the end effector 104 to the distal end of the shaft 102, and a drive housing 108 coupled to the proximal end of the shaft 102. In at least some embodiments, the surgical tool 100 may be designed to be releasably coupled to a robotic surgical system, and the drive housing 108 can include coupling features that releasably couple the surgical tool 100 to the robotic surgical system.

The terms "proximal" and "distal" are defined herein relative to a robotic surgical system having an interface configured to mechanically and electrically couple the surgical tool 100 to a robotic manipulator. The term "proximal" refers to the position of an element closer to the robotic manipulator and the term "distal" refers to the position of an element closer to the end effector 104 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 100, the end effector 104 is configured to move (pivot) relative to the shaft 102 at the wrist 106 to position the end effector 104 at a desired orientation and location relative to a surgical site. The housing 108 includes various mechanisms designed to control operation of various features associated with the end effector 104 (e.g., clamping, firing, rotation, articulation, energy delivery, etc.). In at least some embodiments, the shaft 102, and hence the end effector 104 coupled thereto, is configured to rotate about a longitudinal axis $A_1$ of the shaft 102. In such embodiments, the various mechanisms included in the housing 108 are configured to control the rotational movement of the shaft 102.

The surgical tool 100 can have any of a variety of configurations and can be configured to perform at least one surgical function. For example, the surgical tool 100 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 100 may be configured to apply energy to tissue, such as radiofrequency (RF) energy.

The shaft 102 is an elongate member extending distally from the housing 108 and has at least one lumen extending therethrough along its axial length. The shaft 102 may be fixed to the housing 108, but could alternatively be releasably coupled to the housing 108 to allow the shaft 102 to be interchangeable with other shafts. Consequently, this may allow a single housing 108 to be adaptable to various shafts having different end effectors.

The end effector 104 can have a variety of sizes, shapes, and configurations. In the illustrated embodiment, the end effector 104 comprises a tissue grasper having opposing jaws 110, 112 configured to move between open and closed positions. One or both of the jaws 110, 112 may be configured to pivot at the wrist 106 to move the end effector 104 between the open and closed positions. In other embodiments, however, the end effector 104 may have other configurations, e.g., scissors including a pair of opposed cutting jaws, a babcock including a pair of opposed grasping jaws, a retractor, a hook, a spatula, etc. In yet other embodiments, the end effector 104 may comprise an electro cautery tool (energized monopolar or bipolar energy), a stapler, or a clip applier, without departing from the scope of the disclosure.

The wrist 106 can have any of a variety of configurations. Example embodiments and configurations of the wrist 106 are described in U.S. Patent Pub. No. 2015/0209965 entitled "Compact Robotic Wrist," U.S. Patent Pub. No. 2015/0025549 entitled "Hyperdexterous Surgical System," and U.S. patent application Ser. No. 15/200,283 entitled "Methods, Systems, and Devices for Initializing a Surgical Tool." The wrist 106 generally comprises a joint configured to allow pivoting movement of the end effector 104 relative to the shaft 102, such as a pivot joint at which the jaws 110, 112 are pivotally attached.

Figure 2:
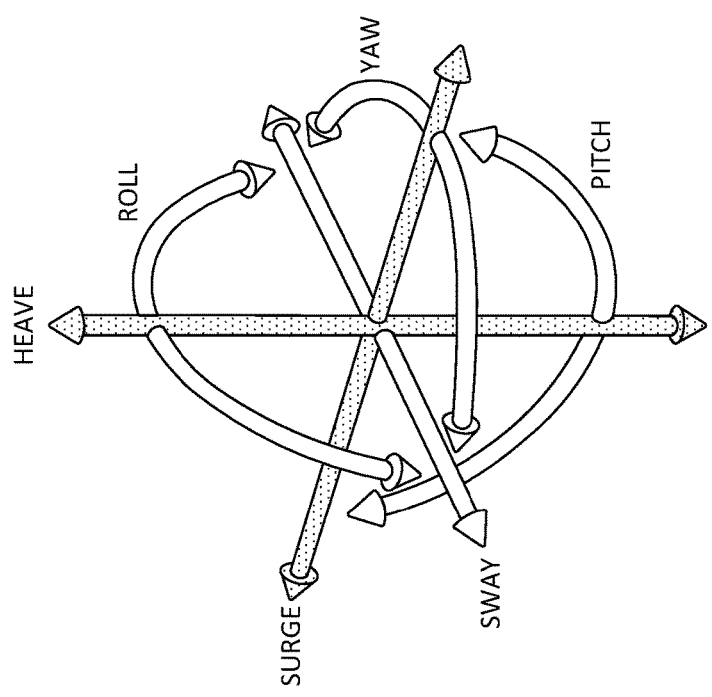
FIG. 2 illustrates potential degrees of freedom in which the wrist of FIG. 1 may be able to articulate (pivot).

FIG. 2 illustrates the potential degrees of freedom in which the wrist 106 may be able to articulate (pivot). The degrees of freedom of the wrist 106 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 104) with respect to a given reference Cartesian frame. As depicted in FIG. 2, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 106 (e.g., X-axis), yaw movement about a second axis of the wrist 106 (e.g., Y-axis), and combinations thereof to allow for 360° rotational movement of the end effector 104 about the wrist 106. In other applications, the pivoting motion can be limited to movement in a single plane, e.g., only pitch movement about the first axis of the wrist 106 or only yaw movement about the second axis of the wrist 106, such that the end effector 104 moves only in a single plane.

Referring again to FIG. 1, the surgical tool 100 includes a plurality of elongate members (obscured in FIG. 1) forming part of a cable driven motion system configured to effect movement (pivoting) of the end effector 104 relative to the shaft 102. The elongate members may be referred to and otherwise characterized as cables, bands, lines, cords, wires, ropes, strings, twisted strings, etc. As used herein, the elongate members used in the surgical tool 100 will be referred to as "drive cables." The drive cables can be made from a variety of materials including, but not limited to, metal (e.g., tungsten, stainless steel, etc.) or a polymer (e.g., VECTRAN®). In some embodiments, the drive cables may be made of any of the aforementioned materials (or any combination thereof) and may be shrouded in a metal housing. Example drive cables are described in previously mentioned U.S. Patent Pub. Nos. 2015/0209965 and 2015/0025549.

The drive cables are operably coupled to various actuation mechanisms housed within the drive housing 108 and extend within the lumen of the shaft 102 to the wrist 106 where they are operably engaged with the end effector 104. Selective actuation of the drive cables causes the end effector 104 (e.g., one or both of the jaws 110, 112) to move (pivot) relative to the shaft 102. More specifically, selective actuation of the drive cables can cause any one or more of the drive cables to translate longitudinally within the lumen of the shaft 102 and thereby cause pivoting movement of the end effector 104. In operation, one or more drive cables may translate longitudinally to cause the end effector 104 to articulate (e.g., both of the jaws 110, 112 angle in a same direction), to cause the end effector 104 to open (e.g., one or both of the jaws 110, 112 move away from the other), or to cause the end effector 104 to close (e.g., one or both of the jaws 110, 112 move toward the other).

Actuation of the drive cables can be accomplished in a variety of ways, such as by triggering an associated actuator operably coupled to or housed within the drive housing 108. Actuation applies tension to (i.e., pulls) the drive cables in a proximal direction to cause the corresponding elongate member to translate and thereby cause the end effector 104 to move (articulate) relative to the shaft 102. When both of the jaws 110, 112 are designed to move to open and close the end effector 104, one or more first drive cables will be operably coupled to the first jaw 110 to move that jaw 110 and one or more second drive cables will be operably coupled to the second jaw 112 to move that jaw 112. When only one of the jaws 110, 112 is configured to move to open and close the end effector 104, one or more drive cables may be operably coupled to the first jaw 110 to move the first jaw 110 relative to the second jaw 112.

Actuating the drive cables moves the end effector 104 between an unarticulated position and an articulated position. The end effector 104 is depicted in FIG. 1 in the unarticulated position where a longitudinal axis $A_2$ of the end effector 104 is substantially aligned with the longitudinal axis $A_1$ of the shaft 102, such that the end effector 104 is at a substantially zero angle relative to the shaft 102. Due to factors such as manufacturing tolerance and precision of measurement devices, the end effector 104 may not be at a precise zero angle relative to the shaft 102 in the unarticulated position, but nevertheless be considered "substantially aligned" thereto. In the articulated position, the longitudinal axes $A_1$, $A_2$ are angularly offset from each other such that the end effector 104 is at a non-zero angle relative to the shaft 102.

The drive housing 108 (alternately referred to as a "puck") may be releasably attached to a tool driver of a robotic surgical system in a variety of ways, such as by clamping thereto, clipping thereto, or slidably mating therewith. The actuation devices housed within the drive housing 108 may be controlled by the robot based on user inputs received via a computer system incorporated into the robot. Accordingly, the user inputs control movement of the drive cables and consequently movement of the end effector 104.

Example tool drivers to which the drive housing 108 may be removably attached are described in previously mentioned U.S. patent application Ser. No. 15/200,283. The drive housing 108 illustrated in FIG. 1 is but one example of a suitable drive housing, and additional embodiments of the drive housing 108 are described in previously mentioned U.S. Patent Pub. Nos. 2015/0209965 and 2015/0025549. Example robotic surgical systems are described in U.S. Pat. No. 8,831,782 entitled "Patient-Side Surgeon Interface for a Teleoperated Surgical Instrument" and previously mentioned U.S. Patent Pub. Nos. 2015/0209965 and 2015/0025549.

Figure 3:
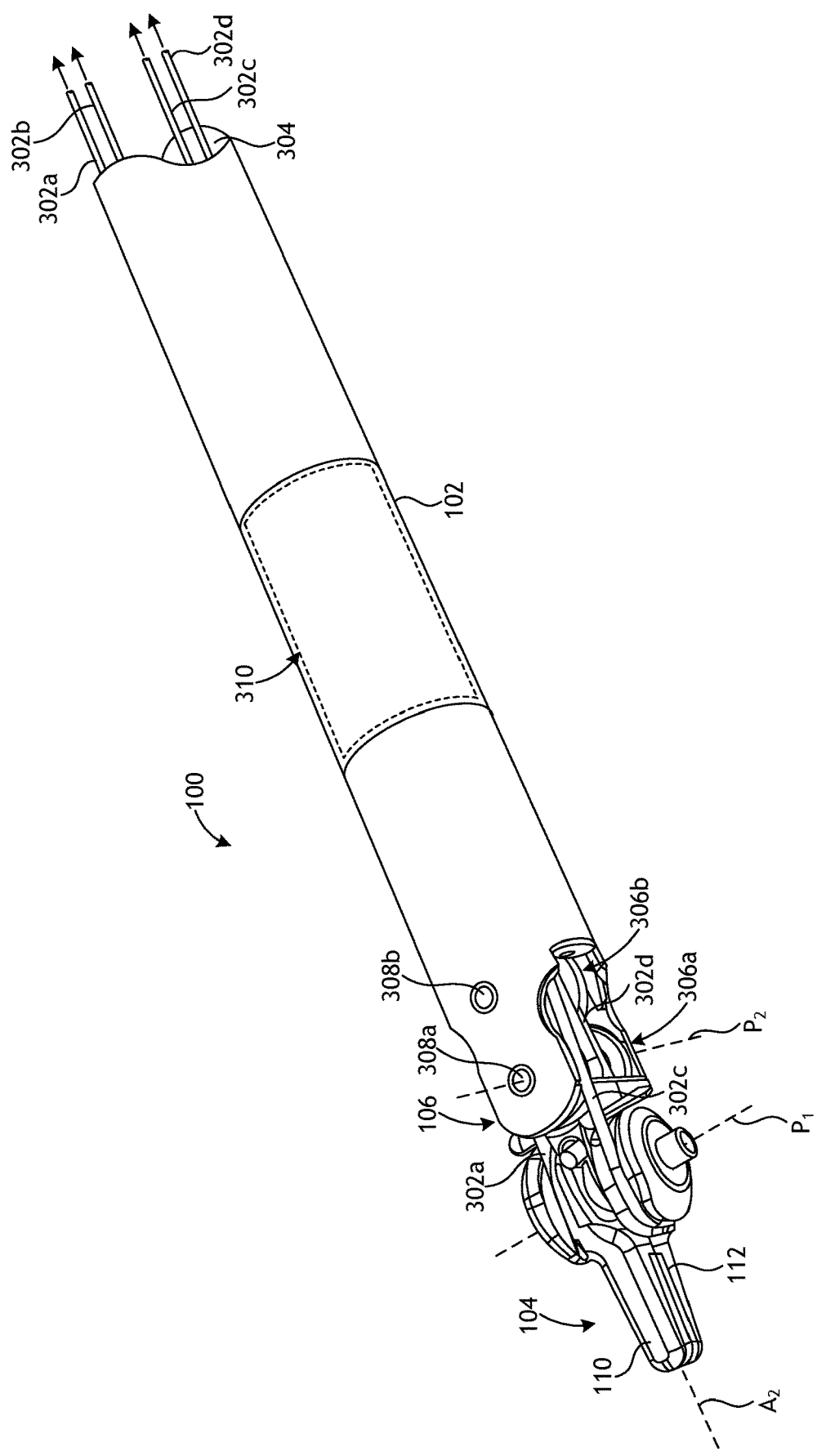
FIG. 3 is an enlarged isometric view of the distal end of the surgical tool of FIG. 1.

FIG. 3 is an enlarged isometric view of the distal end of the surgical tool 100 of FIG. 1. More specifically, FIG. 3 depicts enlarged views of the end effector 104 and the wrist 106, with the end effector 104 in the unarticulated position where the jaws 110, 112 are closed. A plurality of drive cables 302, shown as drive cables 302a, 302b, 302c, and 302d, extend longitudinally within a lumen 304 of the shaft 102 until terminating at the wrist 106. The drive cables 302a-d extend proximally from the end effector 104 to the drive housing 108 (FIG. 1) which, as discussed above, may be configured to facilitate longitudinal movement of the drive cables 302a-d within the lumen 304. The lumen 304 can be a single lumen, as illustrated, or can alternatively comprise a plurality of independent lumens that each receive one of the drive cables 302a-d.

The wrist 106 includes a first plurality of pulleys 306a and a second plurality of pulleys 306b configured to interact with and redirect the drive cables 302a-d. The first plurality of pulleys 306a is mounted to a first wrist axle 308a and the second plurality of pulleys 306b is mounted to a second wrist axle 308b. In at least one embodiment, one pair of drive cables 302a-d is operatively coupled to each of the jaws 110, 112.

The surgical tool 100 has a first pivot axis $P_1$ that is substantially perpendicular to the longitudinal axis $A_2$ of the end effector 104. The jaws 110, 112 are mounted at the first pivot axis P1, thereby allowing the jaws 110, 112 to pivot relative to each other to open and close the end effector 104 or alternatively pivot in tandem to articulate the orientation of the end effector 104. Actuation of the drive cables 302a-d causes relative or tandem movement of the first and second jaws 110, 112 at their respective joints.

The tool 100 may also have a second pivot axis $P_2$ extending through the first wrist axle 308a and about which the end effector 104 is configured to articulate relative to the shaft 102. More particularly, actuation of one or more of the drive cables 302a-d causes movement of the wrist 106 at the second pivot axis $P_2$, and hence articulation of the end effector 104. Consequently, the end effector 104 can articulate with multiple degrees of freedom, e.g., a degree of freedom by articulating about the first pivot axis $P_1$ and another degree of freedom by articulating about the second pivot axis $P_2$. The wrist 106 in this embodiment is pivotable about the second pivot axis $P_2$ in a single plane, e.g., in one of pitch and yaw, and the end effector 104 is pivotable about the first pivot axis $P_1$ in a single, different plane, e.g., the other of pitch and yaw.

According to the present disclosure, the tool 100 may further include a cable tensioner 310 configured to continually compensate for and counteract fatigue (e.g., stretch, creep, slackening, etc.) of the drive cables 302a-d, which can occur, for example, after prolonged usage of the tool 100. Unless properly mitigated, cable fatigue can create backlash in the drive mechanisms used to actuate the drive cables 302a-d. The cable tensioner 310 may be designed to autonomously interact with the drive cables 302a-d to maintain tension in each cable 302a-d during operation, and thereby prevent detrimental drive mechanism backlash.

The cable tensioner 310 may be arranged and otherwise provided at a variety of locations on the tool 100. Suitable locations include any location where the cable tensioner 310 is able to interact with (e.g., engage) one or more of the cables 302a-d. As illustrated in FIG. 3, for example, the cable tensioner 310 may be arranged at or near the distal end of the shaft 102, and the component parts of the cable tensioner 310 may be arranged within the lumen 304 of the shaft 102. This location may prove advantageous in keeping the drive cables 302a-d in tension at or near the wrist 106. In other embodiments, however, the cable tensioner 310 may be arranged at or near the proximal end of the shaft 102 (e.g., adjacent the drive housing 108 of FIG. 1), or may alternatively be arranged at an intermediate location between the proximal and distal ends of the shaft 102. In yet other embodiments, the cable tensioner 310 may be arranged within the drive housing 108 (FIG. 1) and still be able to perform substantially the same function, without departing from the scope of the present disclosure.

Figure 4:
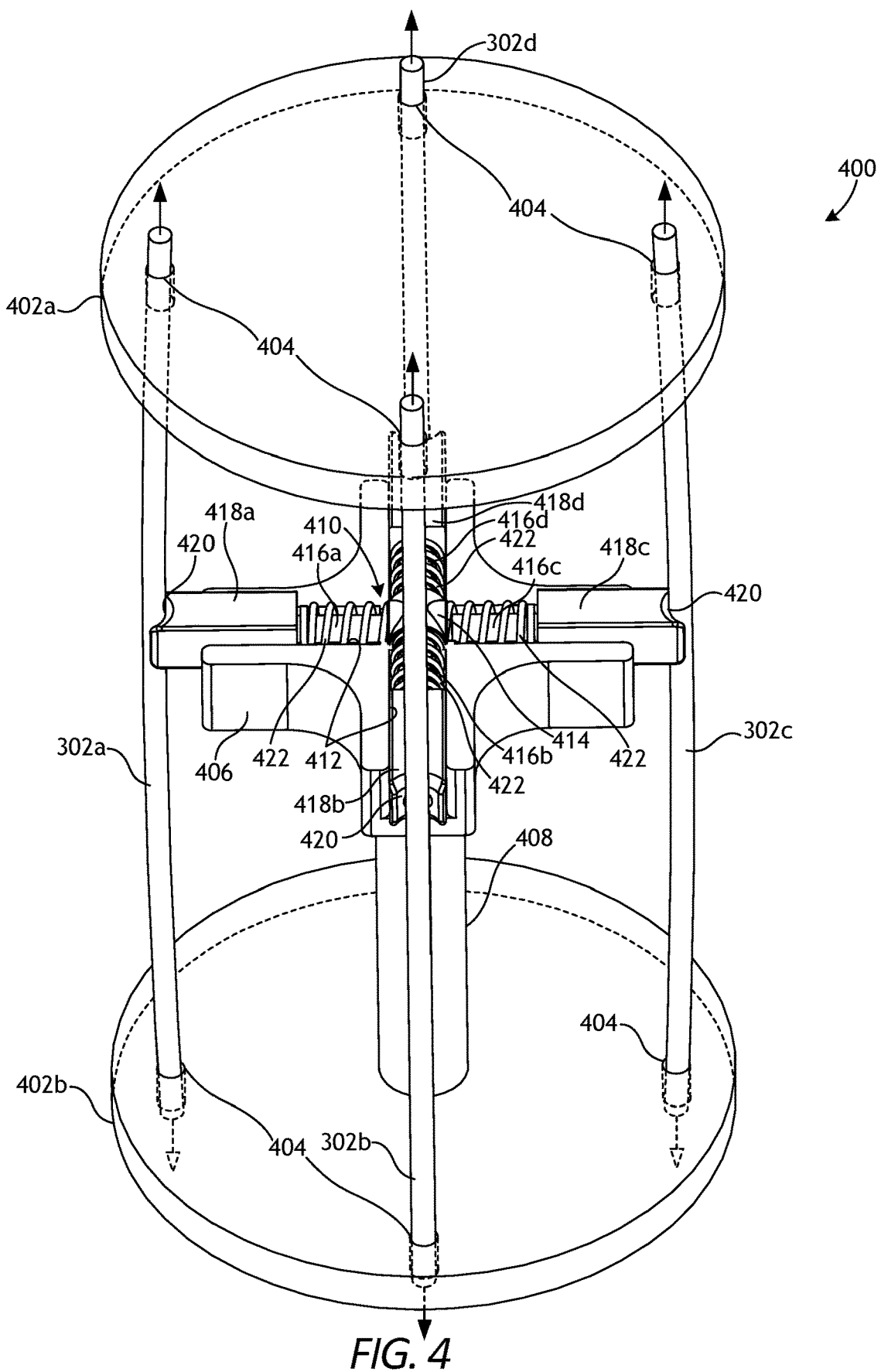
FIG. 4 is an isometric side view of an example cable tensioner.

FIG. 4 is an isometric side view of an example cable tensioner 310, according to one or more embodiments. The cable tensioner 400 may be the same as or similar to the cable tensioner 310 of FIG. 3. As illustrated, the cable tensioner 400 can include a first or "upper" support plate 402a and a second or "lower" support plate 402b axially offset from the first support plate 402a. In some embodiments, as illustrated, the first and second support plates 402a,b may comprise circular discs sized to be received within the lumen 304 (FIG. 3) of the shaft 102 (FIG. 3). In such embodiments, the outer diameter of the support plates 402a,b may be slightly smaller than the inner diameter of the lumen 304 to allow the cable tensioner 400 to be arranged (extended) within the lumen 304. The support plates 402a,b may be secured or otherwise removably coupled to the inner diameter of the lumen 304 via a variety of attachment means including, but not limited to, mechanical fasteners (e.g., screws, bolts, pins, rods, etc.), an interference fit, an adhesive, welding or brazing, or any combination thereof.

While depicted as circular discs, the support plates 402a,b may alternatively exhibit other cross-sectional shapes, such as oval, ovoid, or polygonal shapes, without departing from the scope of the disclosure. Moreover, in at least one embodiment, the first support plate 402a may be omitted from the cable tensioner 400. In such embodiments, the second support plate 402b may independently support the various component parts of the cable tensioner 400, without departing from the scope of the disclosure. In yet other embodiments, both support plates 402a,b may be omitted as long as the various component parts of the cable tensioner 400 can be adequately supported (suspended) within the inner diameter of the lumen 304, without departing from the scope of the disclosure.

Each support plate 402a,b defines a plurality of holes 404 through which the drive cables 302a-d are able to extend. The drive cables 302a-d extend longitudinally from the drive housing 108 (FIG. 1) to the wrist 106 (FIGS. 1 and 3)

within the shaft 102 (FIGS. 1 and 3) and traverse the cable tensioner 400 by passing through the holes 404 in the support plates 402a,b. The proximal and distal ends of each cable 302a-d are omitted in FIG. 4, but the drive cables 302a-d would otherwise extend proximally and distally toward the drive housing 108 and the wrist 106, respectively.

In the illustrated embodiment, each support plate 402a,b defines four holes 404 to receive a corresponding one of the four drive cables 302a-d. Moreover, in the illustrated embodiment, the holes 404 in the first support plate 402a are co-axially aligned (longitudinally) with the holes 404 in the second support plate 402b. In other embodiments, however, the holes 404 in the first support plate 402a may be misaligned with and otherwise angularly offset from the holes 404 in the second support plate 402b, without departing from the scope of the disclosure.

In the illustrated embodiment, the holes 404 are equidistantly spaced from each other on each support plate 402a,b and otherwise angularly offset from each other by approximately 45°. This angular spacing is configured to accommodate the spatial arrangement of the drive cables 302a-d, which may also be equidistantly spaced and otherwise angularly offset from each other by approximately 45°. In other embodiments, however, one or both of the drive cables 302a-d and the holes 404 may be non-equidistantly spaced or angularly offset from an adjacent cable 302a-d or hole 404 by more or less than approximately 45°, without departing from the scope of the disclosure.

The cable tensioner 400 may also include an inner hub 406 supported by a spindle 408 that extends longitudinally between the second support plate 402b and the inner hub 406. In some embodiments, the spindle 408 may be attached to or otherwise rest on the upper surface of the second support plate 402b. In other embodiments, however, the spindle 408 may comprise an integral extension of the second support plate 402b. Likewise, in some embodiments, the spindle 408 may be attached to or otherwise engage the lower surface of the inner hub 406, but in other embodiments the spindle 408 may comprise an integral extension of the inner hub 406, without departing from the scope of the disclosure.

A cable guide assembly 410 is mounted to or otherwise arranged on the inner hub 406. In the illustrated embodiment, the inner hub 406 defines a cavity 412 configured to at least partially receive some or all of the component parts of the cable guide assembly 410. In other embodiments, however, the cavity 412 may be omitted and the cable guide assembly 410 may instead be secured to or otherwise rest on the upper (or lower) surface of the inner hub 406, without departing from the scope of the disclosure.

The cable guide assembly 410 includes a central body 414 having a plurality of guide rails extending laterally (radially) therefrom and referenced as guide rails 416a, 416b, 416c, and 416d. While four guide rails 416a-d are shown in FIG. 4, the number of guide rails 416a-d will generally depend on the number of drive cables 302a-d. Accordingly, in some embodiments, more or less than four guide rails 416a-d may be employed depending on the number of drive cables 302a-d. In some embodiments, the guide rails 416a-d form integral extensions of the central body 414, but may alternatively be coupled or attached to the central body 414 and extend outward therefrom.

In the illustrated embodiment, the guide rails 416a-d are equidistantly spaced from each other about the central body 414 and extend radially outward therefrom at approximately 45° intervals from each angularly adjacent guide rail 416a-d. Accordingly, the central body 414 and guide rails 416a-d of the present embodiment exhibit a general shape or form of an "X" or "cross." Similarly, in the illustrated embodiment, the inner hub 406 is depicted as a four-pronged structure in the general shape or form of an "X" or "cross," and configured to accommodate the similarly shaped central body 414 and guide rails 416a-d. In other embodiments, however, the inner hub 406 need not comprise a four-pronged shape, but could alternatively exhibit a circular or polygonal (e.g., square, rectangular, octagonal, etc.) shape, without departing from the scope of the disclosure.

The cable guide assembly 410 further includes a plurality of cable guides, shown as cable guides 418a, 418b, 418c, and 418d. Each cable guide 418a-d is arranged at the distal end of a corresponding one of the guide rails 416a-d. In some embodiments, each cable guide 418a-d may be configured to receive the distal end of the corresponding guide rail 416a-d. As with the guide rails 416a-d, the number of cable guides 418a-d will depend on the number of drive cables 302a-d.

Each cable guide 418a-d may define and otherwise provide a cable engagement surface 420 configured to engage an outer surface of a corresponding one of the drive cables 302a-d. In the illustrated embodiment, the cable engagement surface 420 comprises an arcuate or concave surface configured to receive or cradle the corresponding adjacent drive cable 302a-d. In other embodiments, the cable engagement surface 420 may alternatively be flat and nonetheless engage the corresponding adjacent drive cable 302a-d. In yet other embodiments, the cable engagement surface 420 may comprise an eyelet or loop that enshrouds the corresponding adjacent drive cable 302a-d, without departing from the scope of the disclosure.

Each cable guide 418a-d may be made of a low-friction material such as a plastic, a metal, a composite material, or any combination thereof. Suitable materials for the cable guides 418a-d include, but are not limited to, stainless steel, nylon, a heat-stable or heat-resistant polymer (e.g., polytetrafluoroethylene [PTFE], polyether ether ketone [PEEK], etc.), an ultra-hard material (e.g., polycrystalline diamond, polycrystalline cubic boron nitride, or impregnated diamond), or any combination thereof. In other embodiments, the cable guides 418a-d may be made of any rigid or semi-rigid material but the cable engagement surface 420 may comprise a low-friction or "lubricious" surface, such as being made of a low friction material or polished to lower its friction coefficient. In yet other embodiments, the cable engagement surface 420 may be coated with a low-friction material, such as TEFLON™ or graphite.

The cable guide assembly 410 further includes a plurality of biasing devices 422 configured to bias the cable guides 418a-d into constant lateral (radial) engagement with a corresponding one of the drive cables 302a-d. In the illustrated embodiment, the biasing devices 422 are depicted as compression springs, but could alternatively comprise a series of Belleville washers, a hydraulic or pneumatic piston assembly, or any combination thereof.

As illustrated, each biasing device 422 extends between the central body 414 and a corresponding one of the cable guides 418a-d, and a corresponding guide rail 416a-d extends through each biasing device 422. Each biasing device 422 exhibits a spring force that continuously urges the corresponding cable guide 418a into lateral (radial) engagement with the drive cables 302a-d and thereby maintains tension in the drive cables 302a-d throughout operation of the tool 100 (FIGS. 1 and 3). As shown in FIG. 4, the spring force can result in the drive cables 302a-d slightly bowing radially outward.

Figure 5A:
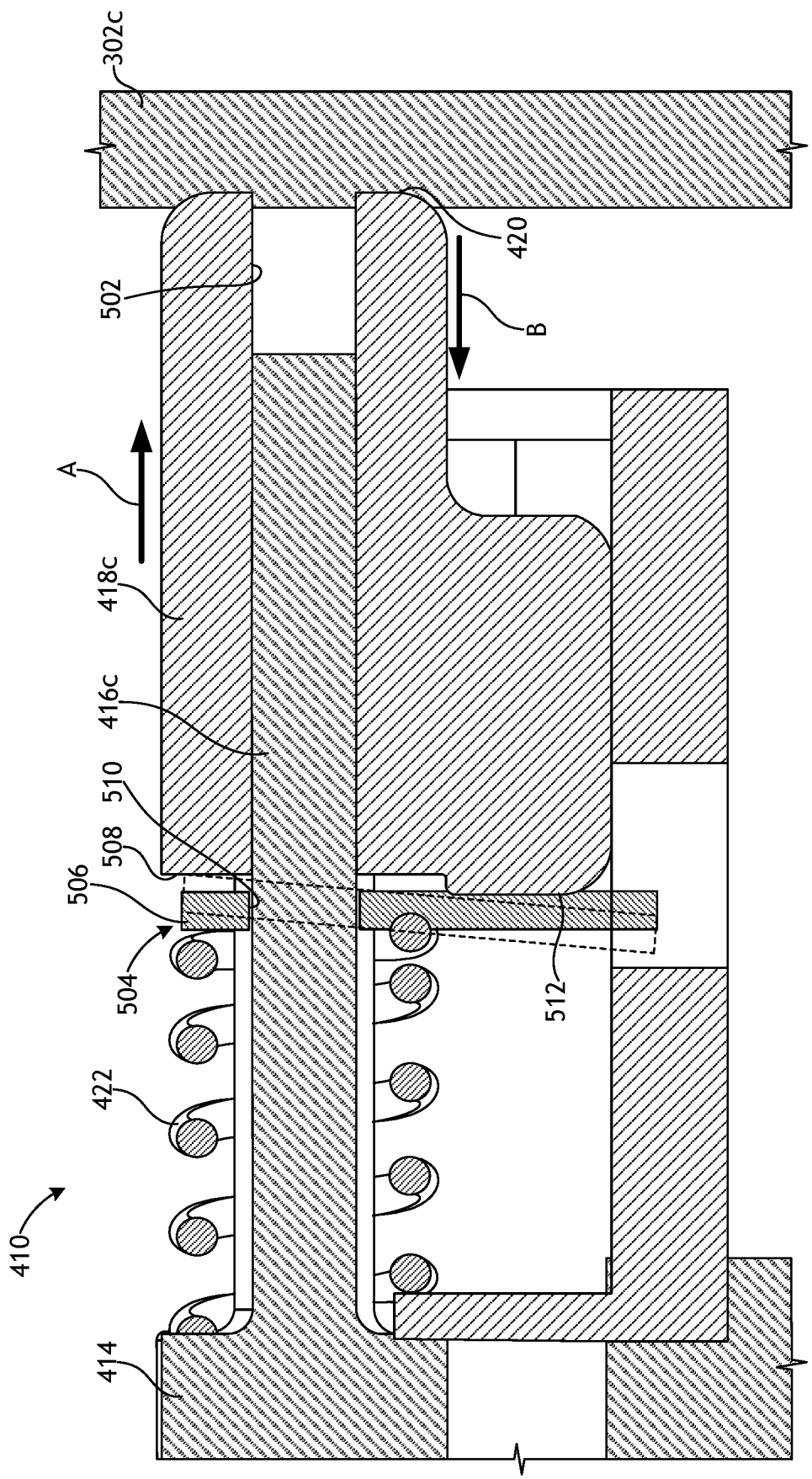
FIG. 5A is an enlarged cross-sectional side view of a portion of the cable guide assembly of FIG. 4 and showing an example locking device.

FIG. 5A is an enlarged cross-sectional side view of a portion of the cable guide assembly 410, according to one or more embodiments. More specifically, FIG. 5A depicts an enlarged cross-sectional side view of the third guide rail 416c, the third cable guide 418c, and an associated biasing device 422. While the following description is directed to operation of the third guide rail 416c and the third cable guide 418c, it will be appreciated that the following description is equally applicable to operation of each guide rail 416a-d and each cable guide 418a-d of the cable guide assembly 410.

As illustrated, the third guide rail 416c is received within a central orifice 502 defined in the third cable guide 418c. The third guide rail 416c may be able to translate within the central orifice 502 or, alternatively stated, the third cable guide 418c may be able to translate relative to the third guide rail 416c. The biasing device 422 extends between the central body 414 and the third cable guide 418c, and helically extends about the outer surface of the third guide rail 416c. The spring force of the biasing device 422 constantly urges the third cable guide 418c into lateral (radial) engagement with the third drive cable 302c at the cable engagement surface 420, which maintains constant tension in the third drive cable 302c.

The cable guide assembly 410 may further include a locking mechanism 504 that prevents the third cable guide 418c from reversing direction. While the biasing device 422 constantly urges the third cable guide 418c in a first direction (shown by arrow A) and into lateral engagement with the third drive cable 302c, the locking mechanism 504 prevents the third cable guide 418c from reversing direction back toward the central body 414 in a second direction (shown by arrow B) opposite the first direction.

In the illustrated embodiment, the locking mechanism 504 comprises a stop plate 506 that interposes the biasing device 422 and a back wall 508 of the third cable guide 418c. A hole 510 is defined through the stop plate 506 and the third guide rail 416c is extendable through the hole 510. The stop plate 506 is pivotable between a sliding position, where the stop plate 506 is able to slide along the third guide rail 416c in the first direction A, and a binding position, where a protrusion 512 defined on the back wall 508 of the third cable guide 418c pivots the stop plate 506 into binding engagement with the outer surface of the third guide rail 416c and thereby prevents the stop plate from moving in the second direction B.

In operation, the biasing device 422 urges the stop plate 506 against the back wall 508 of the third cable guide 418c and thereby forces the third cable guide 418c into constant biased engagement with the third drive cable 302c in the first direction A. When the third drive cable 302c slackens or stretches, the biasing device 422 compensates for the added slack by urging the third cable guide 418c further radially outward in the first direction A relative to the third guide rail 416c. Thus, tension in the third drive cable 302c is continuously maintained during operation. During this time, the stop plate 506 remains in the sliding position, which allows the stop plate 506 to move relative to the third guide rail 416c and push the third cable guide 418c in the first direction A.

The third drive cable 302c may occasionally attempt to "back drive" or push back against the third cable guide 418c in the second direction B during operation. When this occurs, the protrusion 512 pivots the stop plate 506 into the binding position, as shown in dashed lines in FIG. 5A. In the binding position, the stop plate 506 comes into binding engagement with the outer surface of the third guide rail 416c at the hole 510, which stops (prevents) progression of the third cable guide 418c in the second direction B.

Figure 5B:
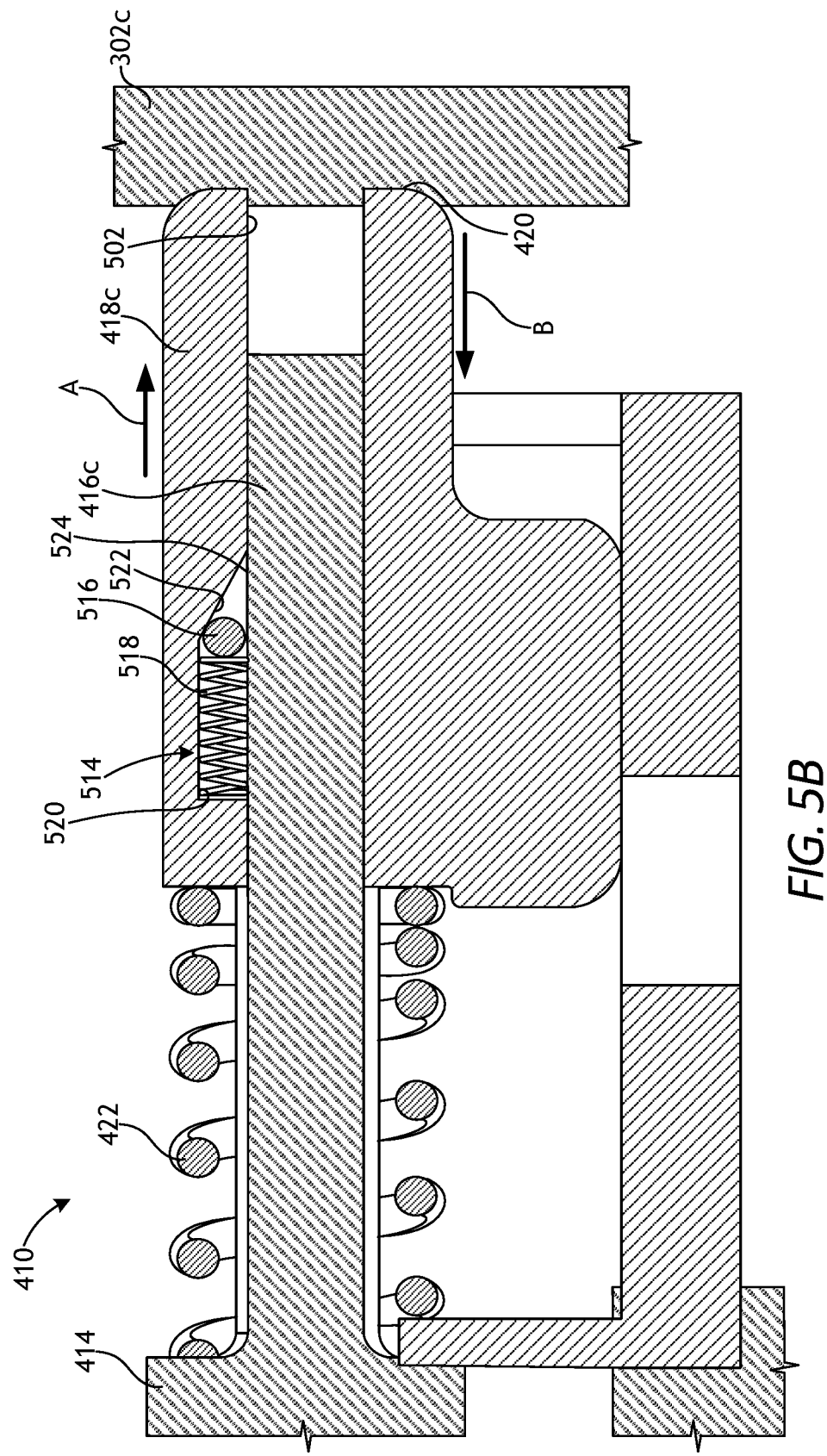
FIG. 5B is another enlarged cross-sectional side view of a portion of the cable guide assembly of FIG. 4 and showing another example locking device.

FIG. 5B is another enlarged cross-sectional side view of a portion of the cable guide assembly 410, according to one or more additional embodiments. Similar to FIG. 5A, FIG. 5B depicts an enlarged cross-sectional side view of the third guide rail 416c, the third cable guide 418c, and the corresponding biasing device 422. Moreover, while the following description is directed to operation of the third guide rail 416c and the third cable guide 418c, it will be appreciated that the description is equally applicable to operation of any of the guide rails 416a-d and cable guides 418a-d of the cable guide assembly 410.

Similar to the embodiment of FIG. 5A, in FIG. 5B the third guide rail 416c is received within the central orifice 502 of the third cable guide 418c, the biasing device 422 extends between the central body 414 and the third cable guide 418c, and helically extends about the outer surface of the third guide rail 416c. Moreover, the spring force of the biasing device 422 constantly urges the third cable guide 418c into lateral (radial) engagement with the third drive cable 302c at the cable engagement surface 420.

Similar to the embodiment of FIG. 5A, the cable guide assembly 410 of FIG. 5B also includes a locking mechanism 514 that operates to prevent the third cable guide 418c from reversing direction. Unlike the locking mechanism 504 of FIG. 5A, the locking mechanism 514 of FIG. 5B comprises a freewheel clutch assembly, such as a sprag clutch or the like. More specifically, the locking mechanism 514 includes a roller bearing 516 and a spring 518 arranged within a pocket 520 defined in the inner diameter of the central orifice 502. The pocket 520 provides a tapered portion 522 and the spring 518 biases the roller bearing 516 into constant engagement with the tapered portion 522.

In operation, the biasing device 422 urges the third cable guide 418c into constant biased engagement with the third drive cable 302c in the first direction A. When the third drive cable 302c slackens or stretches, the biasing device 422 compensates for the slack by urging the third cable guide 418c radially outward relative to the third guide rail 416c even further in the first direction A. Thus, tension in the third drive cable 302c is continuously maintained. As the third cable guide 418c moves relative to the third guide rail 416c, the roller bearing 516 rolls against an outer surface 524 of the third guide rail 416c while the spring 518 maintains the roller bearing 516 in engagement with the tapered portion 522.

When the third drive cable 302c attempts to "back drive" or push back against the third cable guide 418c during operation, the locking mechanism 514 prevents the third drive cable 302c from reversing in the second direction B. More particularly, when the third drive cable 302c pushes back against the third cable guide 418c in the second direction B, the roller bearing 516 becomes wedged between the tapered portion 522 and the outer surface 524 of the third guide rail 416c, which generates a binding engagement against the outer surface 524. This binding engagement stops (prevents) progression of the third guide rail 416c and the third cable guide 418c in the second direction B.

Accordingly, the cable guide assembly 410 embodiments depicted in FIGS. 5A and 5B each provide a self-adjusting constant tension on each of the drive cables 302a-d and autonomously adjust for stretch/creep in the drive cables 302a-d via the spring bias of the biasing devices 422. Furthermore, any back driving loads applied through the drive cables 302a-d are assumed by the anti-reverse capability of the locking mechanisms 504 (FIG. 5A) and 514

(FIG. 5B), which results in a constant tension on the drive cables 302a-d and predictable drive performance of the surgical tool 100 (FIGS. 1 and 3).

Moreover, it should be noted that, in some embodiments, the locking mechanisms 504 (FIG. 5A) and 514 (FIG. 5B) may not be necessary and may otherwise be omitted from the cable tensioner 400, without departing from the scope of the disclosure. In such embodiments, the biasing devices 422 may each exhibit a spring coefficient that is sufficiently large enough to prevent the cable guides 418a-d from reversing direction in the second direction B. In cases where the spring coefficient of the biasing devices 422 is not sufficient, however, the locking mechanisms 504, 514 may be useful.

Figure 6:
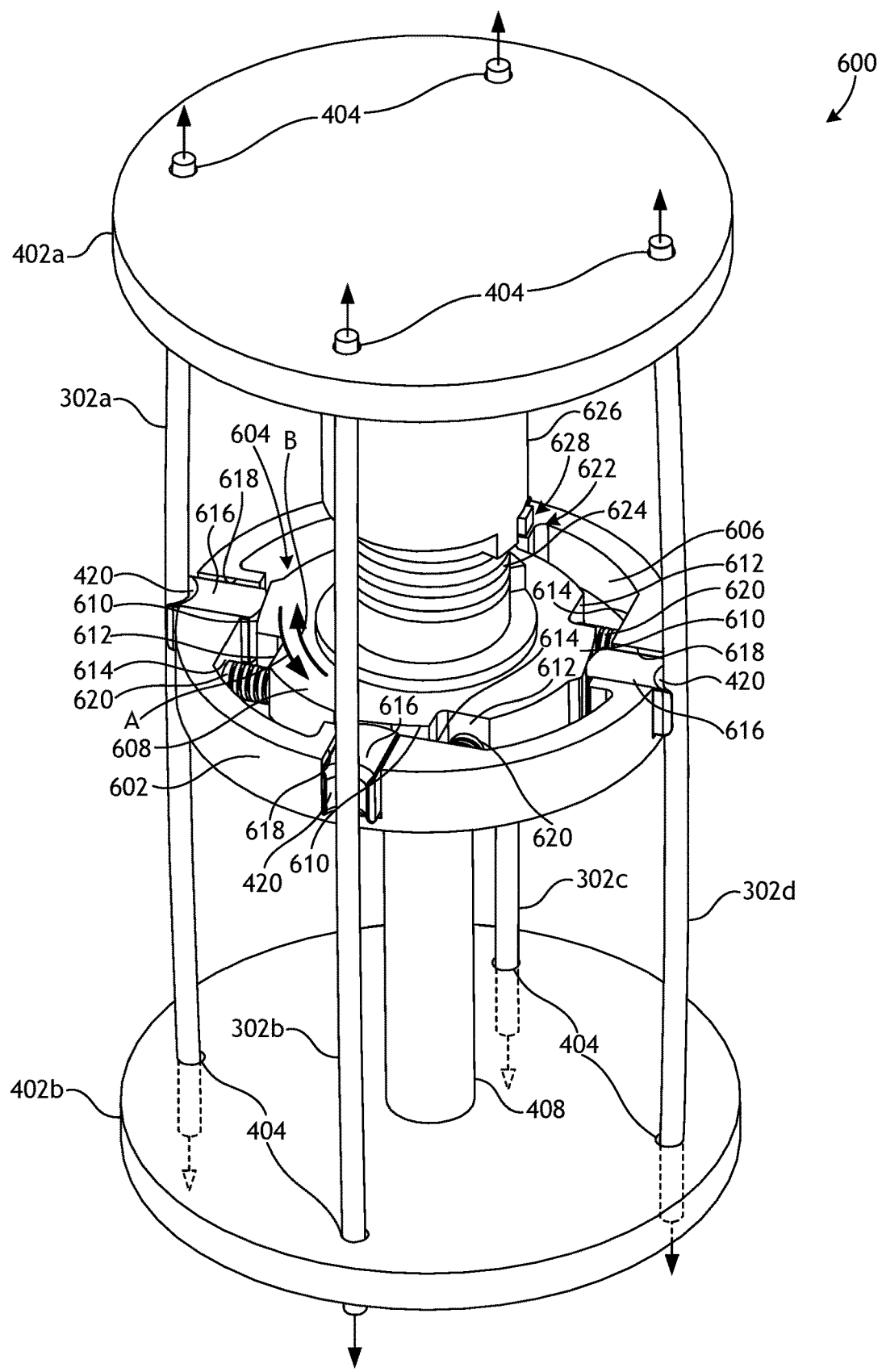
FIG. 6 is an isometric side view of another example cable tensioner.

FIG. 6 is an isometric side view of another example cable tensioner 600, according to one or more additional embodiments. Similar to the cable tensioner 400 of FIG. 4, the cable tensioner 600 may be the same as or similar to the cable tensioner 310 of FIG. 3. Moreover, the cable tensioner 600 may be similar in some respects to the cable tensioner 400 of FIG. 4 and, therefore, similar reference numerals will refer to similar components that may not be described in detail again. Similar to the cable tensioner 400 of FIG. 4, the cable tensioner 600 can include the first and second support plates 402a,b, and each support plate 402a,b has holes 404 through which the drive cables 302a-d are able to pass through.

The cable tensioner 400 also includes an inner hub 602 supported by the spindle 408 that extends longitudinally between the second support plate 402b and the inner hub 602. In the illustrated embodiment, the inner hub 602 is depicted as a generally disc-shaped structure, but could alternatively exhibit a polygonal shape, such as square, rectangular, octagonal, etc.

A cable guide assembly 604 is mounted to or otherwise arranged on the inner hub 602. In the illustrated embodiment, the inner hub 602 defines a cavity 606 configured to at least partially receive some or all of the component parts of the cable guide assembly 604. In other embodiments, however, the cavity 606 may be omitted and the cable guide assembly 604 may instead be secured to or otherwise rest on the upper (or lower) surface of the inner hub 602, without departing from the scope of the disclosure.

The cable guide assembly 604 includes a central body 608, which may be a generally disc-shaped structure. The central body 608 defines or otherwise provides a plurality of cam lobes 610 that extend laterally (radially) from the outer sidewall (e.g., outer diameter) of the central body 608. In some embodiments, as illustrated, the cam lobes 610 form integral extensions of the central body 608. In other embodiments, however, the cam lobes 610 can be attached to the central body 608 at the outer sidewall.

The cam lobes 610 may be configured to angularly align with the drive cables 302a-d. Accordingly, the number of cam lobes 610 may depend on the number of drive cables 302a-d used in the surgical tool 100 (FIGS. 1 and 3). In the illustrated embodiment, the cam lobes 610 are equidistantly spaced from each other about the central body 608 and extend radially outward therefrom at approximately 45° intervals from each angularly adjacent cam lobe 610.

The central body 608 further provides and otherwise defines a plurality of outer biasing surfaces 612 formed on the outer sidewall of the central body 608. In some embodiments, the number of outer biasing surfaces 612 is equal to the number of drive cables 302a-d. In other embodiments, however, the number of outer biasing surfaces 612 may be less than the number of drive cables 302a-d, without departing from the scope of the disclosure.

The inner hub 602 may be formed to provide a plurality of inner biasing surfaces 614. The central body 608 may be positioned within the cavity 606 of the inner hub 602 such that each outer biasing surface 612 of the central body 608 faces (or is otherwise positioned opposite) a corresponding one of the inner biasing surfaces 614 of the inner hub 602. The central body 608 may be rotatably mounted to the inner hub 602 (e.g., within the cavity 606) such that the central body 608 is able to rotate about a central axis relative to the inner hub 602.

The cable guide assembly 604 further includes a plurality of cable guides 616. Each cable guide 616 may be arranged radially adjacent to and configured to engage a corresponding one of the drive cables 302a-d. As with the cam lobes 610, the number of cable guides 616 will generally depend on the number of drive cables 302a-d and, therefore, more or less than four cable guides 616 may be employed if more or less drive cables 302a-d are used. In some embodiments, as illustrated, each cable guide 616 may be arranged within a corresponding guide passage 618 defined by the inner hub 602. The guide passages 618 may communicate with the cavity 606 and allow the cable guides 616 to translate radially inward and outward as acted upon by the cam lobes 610 and the drive cables 302a-d during operation. In other embodiments, however, the guide passages 618 may be omitted and the cable guides 616 may nonetheless be able to translate radially inward and outward as acted upon by the cam lobes 610 and the drive cables 302a-d.

The cable guides 616 may be similar in some respects to the cable guides 418a-d of FIG. 4. For example, each cable guide 616 may include the cable engagement surface 420 that engages the outer surface of a corresponding one of the drive cables 302a-d. Moreover, each cable guide 616 may be made of any of the low-friction materials mentioned herein or otherwise the cable engagement surface 420 may comprise a lubricious surface or be coated with a low-friction material.

The cable guide assembly 604 further includes a plurality of biasing devices 620 configured to indirectly bias the cable guides 616 into constant lateral (radial) engagement with a corresponding one of the drive cables 302a-d. Urging the cable guides 616 into lateral engagement with the drive cables 302a-d maintains tension in the drive cables 302a-d throughout operation of the tool 100 (FIGS. 1 and 3). In the illustrated embodiment, the biasing devices 620 are depicted as compression springs, but could alternatively comprise a series of Belleville washers, a hydraulic or pneumatic piston assembly, or any other type of suitable biasing mechanism.

As illustrated, each biasing device 620 may be arranged within the cavity 606 and interpose opposing outer and inner biasing surfaces 612, 614 of the central body 608 and the inner hub 602, respectively. The spring force of the biasing devices 620 urges the central body 608 to rotate about its central axis in a first angular direction A. As the central body 608 rotates, the cam lobes 610 engage and correspondingly urge the cable guides 616 into lateral (radial) engagement with the drive cables 302a-d. As illustrated, the spring force can result in the drive cables 302a-d slightly bowing radially outward to maintain tension.

Figure 7:
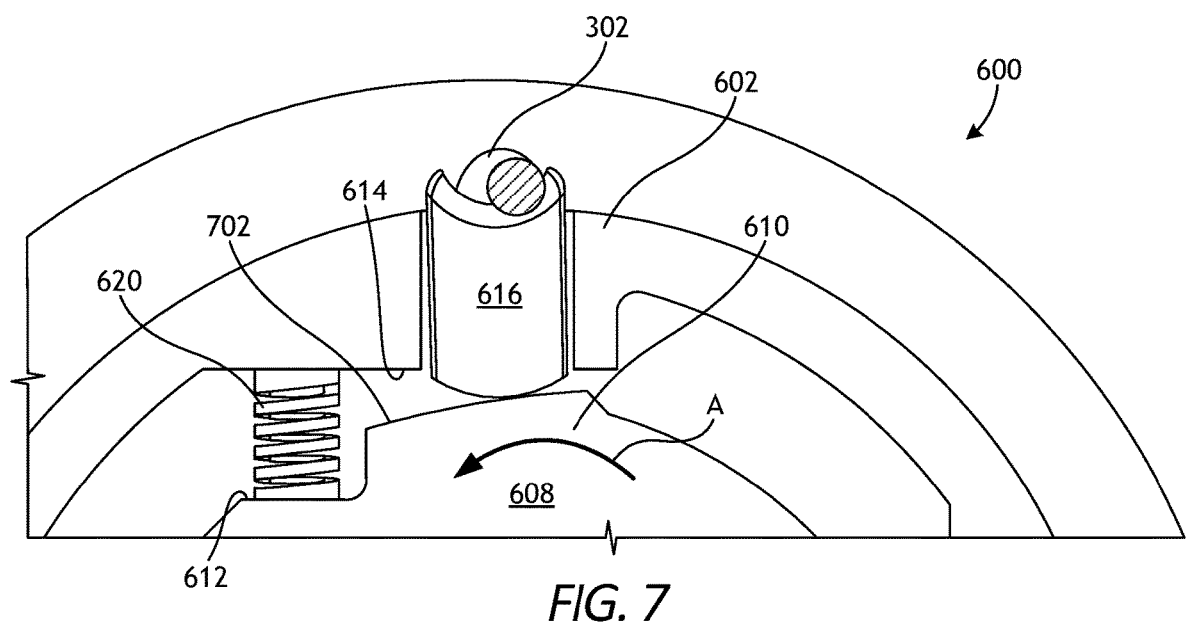
FIG. 7 is an enlarged top view of a portion of the cable tensioner of FIG. 6 to illustrate example operation of maintaining tension in a given drive cable.

FIG. 7 is an enlarged top view of a portion of the cable tensioner 400 to illustrate example operation of maintaining tension in a given drive cable 302, according to one or more embodiments. More specifically, FIG. 7 shows a biasing device 620 arranged to interpose opposing outer and inner biasing surfaces 612, 614 of the central body 608 and the inner hub 602, respectively. The spring force of the biasing device 620 urges the central body 608 to rotate in the first angular direction A, which simultaneously rotates the cam lobe 610 in the same direction. A cam profile 702 is defined on the cam lobe 610 and has a variable diameter that increases in the angular direction. Consequently, as the central body 608 rotates in the first angular direction A, the cam profile 702 correspondingly increases radial engagement against the radially adjacent cable guide 616, which urges the cable guide 616 into lateral (radial) engagement with the drive cable 302.

Referring again to FIG. 6, the cable guide assembly 604 further includes a locking mechanism 622 that prevents the central body 608 from reversing angular direction in a second angular direction B opposite the first angular direction A and thereby prevents back driving of the drive cables 302a-d. In the illustrated embodiment, the locking mechanism 622 comprises a clutch assembly, such as a wrap spring clutch, that allows the central body 608 to rotate in the first angular direction A, but prevents rotation in the second angular direction B. The locking mechanism 622 includes a tension spring 624 and a locking shaft 626. While occluded in FIG. 6, the locking mechanism 622 also includes an inner shaft (not shown) arranged inside the tension spring 624.

The locking shaft 626 extends from the first support plate 402a and is coupled to the tension spring 624. The locking shaft 626 may be coupled to the lower (bottom) surface of the first support plate 402a, or may alternatively comprise an integral extension of the first support plate 402a. Moreover, the locking shaft 626 may be coupled to the tension spring 624 in a variety of ways. In the illustrated embodiment, the locking shaft 626 is coupled to the tension spring 624 via interlocking tabs 628 provided by each of the locking shaft 626 and the tension spring 624. In other embodiments, the locking shaft 626 may be coupled to the tension spring 624 via one or more mechanical fasteners, clamping, welding, an adhesive, an interference fit, a snap fit, or any combination thereof.

During operation, the tension spring 624 rests on the central body 608 and allows the central body 608 to rotate or "slip" in the first angular direction A as acted upon by the biasing devices 620. Rotation in the first angular direction A causes the tension spring 624 to unwind and allows the central body 608 to rotate. When the drive cables 302a-d attempt to "back drive" or push back against the cable guides 616 and the adjacent cam lobes 610, the central body 608 may be urged to rotate in the second angular direction B. When this occurs, the tension spring 624 tightens down on the inner shaft (not shown) arranged within the tension spring 624, which stops rotation of the central body 608 in the second angular direction B.

Accordingly, while the biasing devices 620 constantly urge the central body 608 to rotate in the first angular direction A, which forces the cable guides 616 into lateral engagement with the drive cables 302a-d, the locking mechanism 622 prevents the central body 608 from rotating in the second angular direction B and thereby effectively prevents the cable guides 616 from reversing direction. This maintains constant tension in the drive cables a-d and compensates for any slack or fatigue that may occur.

While the locking mechanism 622 is shown and described as a wrap spring clutch assembly, those skilled in the art will readily recognize that the locking mechanism 622 may comprise a variety of alternative configurations and designs, without departing from the scope of the disclosure. For example, suitable locking mechanisms 622 include, but are not limited to, a friction locking device (e.g., a roller clutch, a sprag clutch, etc.), a pawl and detent system, a gear and detent system, a ratchet and pawl system, and any combination thereof.

It should be noted that, in some embodiments, the locking mechanism 622 may not be necessary and may otherwise be omitted from the cable tensioner 400. In such embodiments, the biasing devices 620 may each exhibit a sufficient spring coefficient that prevents the central body 608 from rotating in the second angular direction B. In cases where the spring coefficient of the biasing devices 620 is not sufficient, however, the locking mechanism 622 may be employed.

Figure 8:
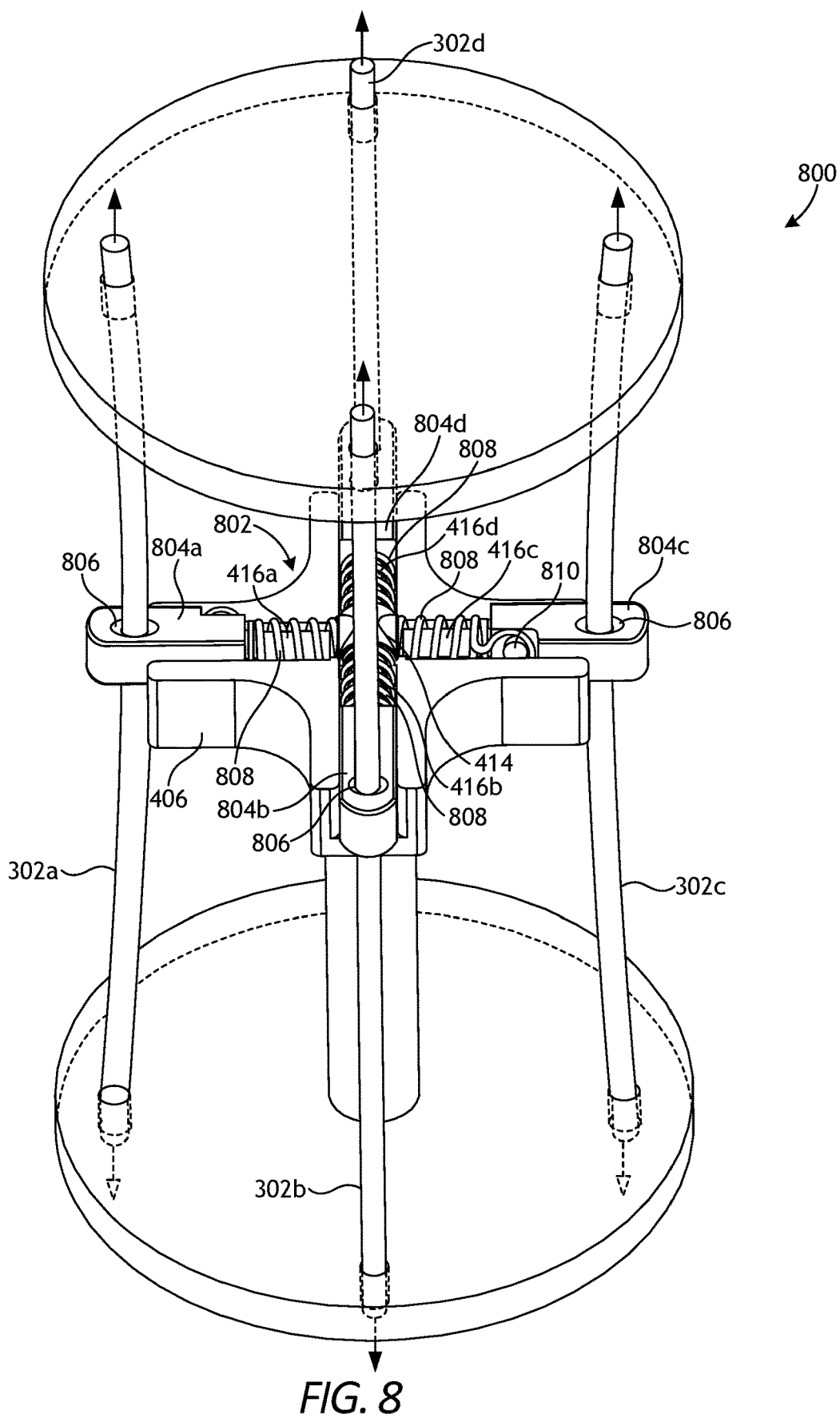
FIG. 8 is an isometric view of another example cable tensioner that provides an inwardly biased force against the drive cables.

The cable tensioners 400 and 600 of FIGS. 4 and 6, respectively, are each designed to provide an outwardly biased force against the drive cables 302a-d to maintain constant tension in the drive cables 302a-d. It is also contemplated herein, however, to have a cable tensioner that provides an inwardly biased force against the drive cables 302a-d to maintain cable tension. FIG. 8, for example, is an isometric view of another example cable tensioner 800 that provides an inwardly biased force against the drive cables 302a-d, according to one or more embodiments. The cable tensioner 800 is similar in some respects to the cable tensioner 400 of FIG. 4 and therefore may be best understood with reference thereto, where similar reference numerals will refer to similar components.

Similar to the cable tensioner 400 of FIG. 4, the cable tensioner 800 includes the inner hub 406 and a cable guide assembly 802 mounted to or otherwise arranged on the inner hub 406. The cable guide assembly 802 includes the central body 414 having the guide rails 416a-d extending laterally (radially) therefrom. A cable guide, shown as cable guides 804a, 804b, 804c, and 804d are again arranged to receive the distal end of each corresponding guide rail 416a-d.

Each cable guide 804a-d may define and otherwise provide a cable engagement surface 806 configured to engage an outer surface of a corresponding one of the drive cables 302a-d. In contrast to the assembly 400 of FIG. 4, the cable engagement surface 806 of each cable guide 804a-d in the assembly 800 comprises an eyelet, an aperture, or a slot configured to receive (capture) the corresponding adjacent drive cable 302a-d. Engagement at the engagement surface 806 is loose enough to allow the corresponding drive cable 302a-d to translate longitudinally without the cable guide 804a-d providing substantive friction resistance that would impede longitudinal movement. Moreover, each cable guide 804a-d and may be made of any of the low-friction materials mentioned herein with respect to the cable guides 418a-d of FIG. 4. Otherwise, or in addition thereto, the cable engagement surface 806 may be coated with a low-friction material, such as TEFLON™ or graphite.

The cable guide assembly 802 further includes a plurality of biasing devices 808 configured to bias the cable guides 804a-d into constant lateral (radial) engagement with a corresponding one of the drive cables 302a-d. As opposed to the biasing devices 422 of FIG. 4, which are designed to apply a compressive load (i.e., radial outward bias), the biasing devices 808 in FIG. 8 may comprise coil springs or another type of biasing mechanism that is designed to apply a tensile load (i.e., radial inward bias).

As illustrated, each biasing device 808 extends between the central body 414 and a corresponding one of the cable guides 804a-d, and a corresponding guide rail 416a-d extends through each biasing device 808. Each biasing device 808 may be coupled to each of the central body 414 and the corresponding cable guides 804a-d and may exhibit a spring force that continuously pulls the corresponding cable guide 804a-d and associated drive cable 302a-d radially inward. In at least one embodiment, as illustrated, the biasing devices 808 may be coupled to the associated cable guide 804*a-d* at a pin 810 (one shown) or other suitable attachment feature. Continuously pulling the drive cables 302*a-d* radially inward helps to maintain tension in the drive cables 302*a-d* throughout operation of the tool 100 (FIGS. 1 and 3). As shown in FIG. 8, the spring force of the biasing devices 808 can result in the drive cables 302*a-d* slightly bowing radially inward.

Embodiments disclosed herein include:

A. A surgical tool that includes a drive housing, an elongate shaft that extends from the drive housing and defines a lumen, a plurality of drive cables extending within the lumen between the drive housing and an end effector, and a cable tensioner including an inner hub and a cable guide assembly that comprises a central body mounted on the inner hub, a plurality of cable guides engageable with the plurality of drive cables, where each cable guide is arranged to engage a corresponding one of the plurality of drive cables, and one or more biasing devices engageable with the central body to bias the plurality of cable guides into constant engagement with the plurality of drive cables and thereby maintain constant tension in the plurality of drive cables.

B. A cable tensioner for a surgical tool operable with a plurality of drive cables, the cable tensioner including an inner hub, and a cable guide assembly that comprises a central body mounted on the inner hub, a plurality of cable guides engageable with the plurality of drive cables, where each cable guide is arranged to engage a corresponding one of the plurality of drive cables, and one or more biasing devices engageable with the central body to bias the plurality of cable guides into constant engagement with the plurality of drive cables and thereby maintain constant tension in the plurality of drive cables.

C. A method of operating a surgical tool that includes triggering actuation of one or more actuation devices in a drive housing and thereby moving one or more of a plurality of drive cables extending within a lumen of an elongate shaft extending from the drive housing, and maintaining tension in the plurality of drive cables with a cable tensioner, the cable tensioner including an inner hub and a cable guide assembly that comprises a central body mounted on the inner hub, a plurality of cable guides engageable with the plurality of drive cables, where each cable guide is arranged to engage a corresponding one of the plurality of drive cables, and one or more biasing devices engageable with the central body to bias the plurality of cable guides into constant engagement with the plurality of drive cables and thereby maintain constant tension in the plurality of drive cables.

Each of embodiments A, B, and C may have one or more of the following additional elements in any combination: Element 1: wherein the cable tensioner further includes a support plate and a spindle that extends between the support plate and the inner hub to support the inner hub. Element 2: wherein the support plate is a first support plate and the cable tensioner further comprises a second support plate axially offset from the first support plate, and wherein the first and second support plates each define a plurality of holes through which the plurality of drive cables are extendable. Element 3: wherein the cable guide assembly further comprises a plurality of guide rails extending laterally from the central body, and a corresponding one of the plurality of cable guides is received at a distal end of each guide rail, and wherein a corresponding one of the one or more biasing devices extends between the central body and each cable guide to urge each cable guide in a first direction and into constant engagement with the plurality of drive cables. Element 4: wherein the cable guide assembly further comprises a locking mechanism that allows the plurality of cable guides to move in the first direction and simultaneously prevents the plurality of cable guides from moving in a second direction opposite the first direction. Element 5: wherein the central body provides an outer biasing surface and defines a plurality of cam lobes engageable with the plurality of cable guides, and wherein the inner hub provides an inner biasing surface and one of the one or more biasing devices interposes the outer and inner biasing surfaces to urge the central body to rotate in a first angular direction and thereby force the plurality of cam lobes to engage and urge the plurality of cable guides into constant engagement with the plurality of drive cables. Element 6: wherein the cable guide assembly further comprises a locking mechanism that allows the central body to rotate in the first angular direction and simultaneously prevents the central body from rotating in a second angular direction opposite the first angular direction. Element 7: wherein the locking mechanism is selected from the group consisting of a clutch assembly, a friction locking device, a pawl and detent system, a gear and detent system, a ratchet and pawl system, and any combination thereof.

Element 8: further comprising a support plate axially offset from the inner hub and a spindle that extends between the support plate and the inner hub to support the inner hub. Element 9: wherein each cable guide comprises a low-friction material selected from the group consisting of nylon, stainless steel, a heat-stable or heat-resistant polymer, an ultra-hard material, a composite material, and any combination thereof. Element 10: wherein each cable guide provides a cable engagement surface that is coated with a low-friction material. Element 11: wherein the cable guide assembly further comprises a plurality of guide rails extending laterally from the central body and a corresponding one of the plurality of cable guides is received at a distal end of each guide rail, and wherein a corresponding one of the one or more biasing devices extends between the central body and each cable guide to urge the plurality of cable guides in a first direction and into constant engagement with the plurality of drive cables. Element 12: wherein the cable guide assembly further comprises a locking mechanism that includes a stop plate pivotable between a sliding position, where the stop plate allows the corresponding one of the one or more biasing devices to move a corresponding one of the one or more cable guides in the first direction, and a binding position, where the stop plate binds against an outer surface of a corresponding one of the plurality guide rails and thereby stops the corresponding one of the plurality of cable guides from moving in the second direction. Element 13: wherein the cable guide assembly further comprises a locking mechanism that includes a freewheel clutch assembly, the freewheel clutch assembly having a roller bearing that allows the plurality of cable guides to move in the first direction, and becomes wedged against an outer surface of a corresponding one of the plurality of guide rails to stop a corresponding one of the plurality of cable guides from moving in the second direction. Element 14: wherein the central body provides at an outer biasing surface and defines a plurality of cam lobes engageable with the plurality of cable guides, and wherein the inner hub provides an inner biasing surface and one of the one or more biasing devices interposes the outer and inner biasing surfaces to urge the central body to rotate in a first angular direction and thereby force the plurality of cam lobes to engage and urge the plurality of cable guides into constant engagement with the plurality of drive cables. Element 15: wherein the cable guide assembly further comprises a locking mechanism that allows the central body to rotate in the first angular direction and simultaneously prevents the central body from rotating in a second angular direction opposite the first angular direction. Element 16: wherein the locking mechanism is a clutch assembly and the cable tensioner further comprises a first support plate axially offset from the inner hub and a spindle that extends between the first support plate and the inner hub to support the inner hub, a second support plate axially offset from the first support plate, a tension spring that rests on the central body, and a locking shaft that extends from the second support plate and is coupled to the tension spring, wherein the tension spring allows the central body to rotate in the first angular direction as acted upon by the one or more biasing devices, but tightens and thereby prevents the central body from rotating in the second angular direction when the plurality of drive cables push back against the plurality of cable guides.

Element 17: further comprising allowing the plurality of cable guides to move in a first direction to maintain constant tension in the plurality of drive cables, and preventing the plurality of cable guides from moving in a second direction opposite the first direction with a locking mechanism.

By way of non-limiting example, exemplary combinations applicable to A, B, and C include: Element 1 with Element 2; Element 3 with Element 4; Element 5 with Element 6; Element 6 with Element 7; Element 11 with Element 12; Element 11 with Element 13; Element 14 with Element 15; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing;
    an elongate shaft that extends from the drive housing and defines a lumen;
    a plurality of drive cables extending within the lumen between the drive housing and an end effector; and
    a cable tensioner including an inner hub and a cable guide assembly that comprises:
        a central body mounted on the inner hub;
        a plurality of cable guides engageable with the plurality of drive cables, where each cable guide engages and provides a radial load on a corresponding one of the plurality of drive cables; and
        one or more biasing devices engageable with the central body to bias the plurality of cable guides into constant radial engagement with the plurality of drive cables and thereby maintain constant tension in the plurality of drive cables.

2. The surgical tool of claim 1, wherein the cable tensioner further includes a support plate and a spindle that extends between the support plate and the inner hub to support the inner hub.

3. The surgical tool of claim 2, wherein the support plate is a first support plate and the cable tensioner further comprises a second support plate axially offset from the first support plate, and wherein the first and second support plates each define a plurality of holes through which the plurality of drive cables are extendable.

4. The surgical tool of claim 1, wherein the cable guide assembly further comprises a plurality of guide rails extending laterally from the central body, and a corresponding one of the plurality of cable guides is received at a distal end of each guide rail, and
    wherein a corresponding one of the one or more biasing devices extends between the central body and each cable guide to urge each cable guide in a first direction and into constant engagement with the plurality of drive cables.

5. The surgical tool of claim 4, wherein the cable guide assembly further comprises a locking mechanism that allows the plurality of cable guides to move in the first direction and simultaneously prevents the plurality of cable guides from moving in a second direction opposite the first direction.

6. The surgical tool of claim 1, wherein the central body provides an outer biasing surface and defines a plurality of cam lobes engageable with the plurality of cable guides, and
    wherein the inner hub provides an inner biasing surface and one of the one or more biasing devices interposes the outer and inner biasing surfaces to urge the central body to rotate in a first angular direction and thereby force the plurality of cam lobes to engage and urge the plurality of cable guides into constant engagement with the plurality of drive cables.

7. The surgical tool of claim 6, wherein the cable guide assembly further comprises a locking mechanism that allows the central body to rotate in the first angular direction and simultaneously prevents the central body from rotating in a second angular direction opposite the first angular direction.

8. The surgical tool of claim 7, wherein the locking mechanism is selected from the group consisting of a clutch assembly, a friction locking device, a pawl and detent system, a gear and detent system, a ratchet and pawl system, and any combination thereof.

9. A cable tensioner for a surgical tool operable with a plurality of drive cables, the cable tensioner comprising:
   an inner hub; and
   a cable guide assembly that comprises:
      a central body mounted on the inner hub;
      a plurality of cable guides engageable with the plurality of drive cables, where each cable guide engages and provides a radial load on a corresponding one of the plurality of drive cables; and
      one or more biasing devices engageable with the central body to bias the plurality of cable guides into constant radial engagement with the plurality of drive cables and thereby maintain constant tension in the plurality of drive cables.

10. The cable tensioner of claim 9, further comprising a support plate axially offset from the inner hub and a spindle that extends between the support plate and the inner hub to support the inner hub.

11. The cable tensioner of claim 9, wherein each cable guide comprises a low-friction material selected from the group consisting of nylon, stainless steel, a heat-stable or heat-resistant polymer, an ultra-hard material, a composite material, and any combination thereof.

12. The cable tensioner of claim 9, wherein each cable guide provides a cable engagement surface that is coated with a low-friction material.

13. The cable tensioner of claim 9, wherein the cable guide assembly further comprises a plurality of guide rails extending laterally from the central body and a corresponding one of the plurality of cable guides is received at a distal end of each guide rail, and
   wherein a corresponding one of the one or more biasing devices extends between the central body and each cable guide to urge the plurality of cable guides in a first direction and into constant engagement with the plurality of drive cables.

14. The cable tensioner of claim 13, wherein the cable guide assembly further comprises a locking mechanism that includes a stop plate pivotable between a sliding position, where the stop plate allows the corresponding one of the one or more biasing devices to move a corresponding one of the one or more cable guides in the first direction, and a binding position, where the stop plate binds against an outer surface of a corresponding one of the plurality guide rails and thereby stops the corresponding one of the plurality of cable guides from moving in the second direction.

15. The cable tensioner of claim 13, wherein the cable guide assembly further comprises a locking mechanism that includes a freewheel clutch assembly, the freewheel clutch assembly having a roller bearing that allows the plurality of cable guides to move in the first direction, and becomes wedged against an outer surface of a corresponding one of the plurality of guide rails to stop a corresponding one of the plurality of cable guides from moving in the second direction.

16. The cable tensioner of claim 9, wherein the central body provides at an outer biasing surface and defines a plurality of cam lobes engageable with the plurality of cable guides, and
   wherein the inner hub provides an inner biasing surface and one of the one or more biasing devices interposes the outer and inner biasing surfaces to urge the central body to rotate in a first angular direction and thereby force the plurality of cam lobes to engage and urge the plurality of cable guides into constant engagement with the plurality of drive cables.

17. The cable tensioner of claim 16, wherein the cable guide assembly further comprises a locking mechanism that allows the central body to rotate in the first angular direction and simultaneously prevents the central body from rotating in a second angular direction opposite the first angular direction.

18. The cable tensioner of claim 17, wherein the locking mechanism is a clutch assembly and the cable tensioner further comprises:
   a first support plate axially offset from the inner hub and a spindle that extends between the first support plate and the inner hub to support the inner hub;
   a second support plate axially offset from the first support plate;
   a tension spring that rests on the central body; and
   a locking shaft that extends from the second support plate and is coupled to the tension spring,
   wherein the tension spring allows the central body to rotate in the first angular direction as acted upon by the one or more biasing devices, but tightens and thereby prevents the central body from rotating in the second angular direction when the plurality of drive cables push back against the plurality of cable guides.

19. A method of operating a surgical tool, comprising:
   triggering actuation of one or more actuation devices in a drive housing and thereby moving one or more of a plurality of drive cables extending within a lumen of an elongate shaft extending from the drive housing; and
   placing a radial load on each drive cable with a cable tensioner and thereby maintaining tension in the plurality of drive cables, the cable tensioner including an inner hub and a cable guide assembly that comprises:
      a central body mounted on the inner hub;
      a plurality of cable guides engageable with the plurality of drive cables, where each cable guide engages and provides the radial load on a corresponding one of the plurality of drive cables; and
      one or more biasing devices engageable with the central body to bias the plurality of cable guides into constant radial engagement with the plurality of drive cables and thereby maintain constant tension in the plurality of drive cables.

20. The method of claim 19, further comprising:
   allowing the plurality of cable guides to move in a first direction to maintain constant tension in the plurality of drive cables; and
   preventing the plurality of cable guides from moving in a second direction opposite the first direction with a locking mechanism.

* * * * *